US010213147B2

(12) United States Patent
Gallagher et al.

(10) Patent No.: US 10,213,147 B2
(45) Date of Patent: *Feb. 26, 2019

(54) METHOD AND SYSTEMS FOR DETECTING FROM BIOMETRICS THAT PERSON SITTING IN SEAT OF VEHICLE REQUIRES MEDICAL ATTENTION AND FOR PROVIDING MEDICAL ATTENTION TO THE PERSON

(71) Applicant: Lear Corporation, Southfield, MI (US)

(72) Inventors: David Gallagher, Sterling Heights, MI (US); Francesco Migneco, Salene, MI (US); Arjun Yetukuri, Rochester Hills, MI (US); Karl Henn, New Hudson, MI (US); Gerald Patrick, Shelby Township, MI (US)

(73) Assignee: Lear Corporation, Southfield, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/043,670

(22) Filed: Jul. 24, 2018

(65) Prior Publication Data
US 2018/0333093 A1 Nov. 22, 2018

Related U.S. Application Data

(63) Continuation of application No. 15/599,631, filed on May 19, 2017, now Pat. No. 10,034,631.

(51) Int. Cl.
*G08B 1/08* (2006.01)
*A61B 5/18* (2006.01)
(Continued)

(52) U.S. Cl.
CPC ............... *A61B 5/18* (2013.01); *A61B 5/024* (2013.01); *A61B 5/0205* (2013.01);
(Continued)

(58) Field of Classification Search
CPC ....... A61B 5/18; A61B 5/0205; A61B 5/6893; A61B 5/024; A61B 5/1118; A61B 5/4809; B60N 2/0276; B60N 2002/4485
(Continued)

(56) References Cited

U.S. PATENT DOCUMENTS 6,506,153 B1 1/2003 Littek et al.
6,682,494 B1 1/2004 Sleichter, III et al.
(Continued)

FOREIGN PATENT DOCUMENTS

CN 2855822 Y 1/2007
CN 203186154 U 9/2013
(Continued)

*Primary Examiner* — Tanmay K Shah
(74) *Attorney, Agent, or Firm* — Brooks Kushman P.C.

(57) ABSTRACT

A method for a vehicle includes using sensors in a vehicle seat to detect biometrics of a person sitting in the seat and a vehicle controller determining from the biometrics of the person whether the person requires medical attention. In response to the person requiring medical attention, a request for assistance for the person is broadcasted via a V2X transceiver of the vehicle to medical practitioners of a medical practitioner network who are near a location of vehicle during the broadcasting. The medical practitioner network includes the person as a subscriber and medical practitioners as providers. Alternately, in response to the person requiring medical attention, the vehicle controller uses an autonomous vehicle control system of the vehicle to drive the vehicle to a medical facility.

20 Claims, 4 Drawing Sheets

(51) Int. Cl.
  *B60N 2/02* (2006.01)
  *A61B 5/0205* (2006.01)
  *A61B 5/00* (2006.01)
  *A61B 5/024* (2006.01)
  *A61B 5/11* (2006.01)
  *B60N 2/90* (2018.01)

(52) U.S. Cl.
  CPC .......... *A61B 5/6893* (2013.01); *B60N 2/0276* (2013.01); *A61B 5/1118* (2013.01); *B60N 2002/981* (2018.02)

(58) Field of Classification Search
  USPC ...................................................... 340/539.1
  See application file for complete search history.

(56) References Cited

U.S. PATENT DOCUMENTS

| | | | |
|---|---|---|---|
| 7,219,923 B2 | 5/2007 | Fujita et al. | |
| 7,731,279 B2 | 6/2010 | Asada et al. | |
| 7,808,395 B2 | 10/2010 | Raisanen et al. | |
| 8,706,204 B2 | 4/2014 | Seo et al. | |
| 8,710,784 B2 | 4/2014 | Meyer et al. | |
| 8,725,311 B1 | 5/2014 | Breed | |
| 8,971,839 B2 | 3/2015 | Hong | |
| 8,979,191 B2 | 3/2015 | Friderich et al. | |
| 8,989,697 B2 | 3/2015 | Leung et al. | |
| 9,237,242 B2 | 1/2016 | Basir | |
| 9,272,689 B2 | 3/2016 | Fung et al. | |
| 9,277,385 B2 | 3/2016 | Iwamoto | |
| 2004/0119599 A1 | 6/2004 | Stevenson et al. | |
| 2005/0016786 A1* | 1/2005 | Mack | B60N 2/002 180/271 |
| 2013/0234826 A1 | 9/2013 | Sekiguchi et al. | |
| 2014/0361871 A1* | 12/2014 | Silva | A61B 5/04012 340/5.52 |
| 2015/0266405 A1 | 9/2015 | Fitzpatrick et al. | |
| 2016/0001781 A1 | 1/2016 | Fung et al. | |
| 2016/0278709 A1 | 9/2016 | Ridao Granado et al. | |
| 2017/0193811 A1* | 7/2017 | Stowell | G08C 17/02 |

FOREIGN PATENT DOCUMENTS

| | | |
|---|---|---|
| WO | 2015127193 A1 | 8/2015 |
| WO | 2016099299 A1 | 6/2016 |

* cited by examiner

METHOD AND SYSTEMS FOR DETECTING FROM BIOMETRICS THAT PERSON SITTING IN SEAT OF VEHICLE REQUIRES MEDICAL ATTENTION AND FOR PROVIDING MEDICAL ATTENTION TO THE PERSON

CROSS-REFERENCE TO RELATED APPLICATIONS

This application is a continuation of U.S. application Ser. No. 15/599,631, filed May 19, 2017, now U.S. Pat. No. 10,034,631; the disclosure of which is hereby incorporated in its entirety by reference herein.

TECHNICAL FIELD

The present invention relates to a vehicle seat system configured to monitor or sense presence, physiological attributes, conditions, and/or states of a person sitting in a vehicle seat.

BACKGROUND

Approaches to monitor the physiological state of a person include attaching adhesive electrodes to the skin of the person. These approaches are cumbersome and are not suitable for use with vehicular applications involving a person sitting in a vehicle seat of an operating vehicle.

SUMMARY

A method for a vehicle is provided. The method includes establishing a medical practitioner network having as a subscriber to the medical practitioner network a person that is sitting in a seat of the vehicle and having as providers of the medical practitioner network a plurality of medical practitioners. The method further includes detecting, from one or more sensors in the seat of the vehicle, biometrics of the person and determining from the biometrics of the person, by a vehicle controller in communication with the one or more sensors, whether the person requires medical attention. In response to the vehicle controller determining from the biometrics of the person that the person requires medical attention, a request for assistance for the person is broadcasted, from a V2X transceiver of the vehicle, to medical practitioners of the medical practitioner network who are near a location of vehicle during the broadcasting.

The location of the vehicle and/or the biometrics of the person may be broadcasted from the V2X transceiver with the request for assistance.

The method may include receiving, by the V2X transceiver, a response from a medical practitioner responding to the request for assistance.

The method may include transmitting to the responding medical practitioner, by the V2X transceiver, the location of the vehicle and/or the biometrics of the person.

The method may further include receiving, by the V2X transceiver, a recommended course of action from the responding medical practitioner and communicating the recommended course of action, by the vehicle controller, to the person. When the vehicle has an autonomous vehicle control system and the recommended course of action is that the person be taken to an emergency room, the method may further include using the autonomous vehicle control system, by the vehicle controller, to drive the vehicle to an emergency room. When the recommended course of action is a prescription for the person, the method may further include employing navigation information from a navigation system of the vehicle, by the vehicle controller, to advise the person of pharmacies near the location of the vehicle. When the recommended course of action is an in-person visit with the responding medical practitioner, the method may further include communicating between the person and the responding medical practitioner a mutually feasible location to meet.

The method may include determining from the biometrics of the person, by the vehicle controller, that the person requires medical attention includes transmitting, via a transceiver of the vehicle, the biometrics of the person to a remote diagnostic facility for the remote diagnostic facility to analyze the biometrics of the person.

The one or more sensors may be piezoelectric sensors.

A system for a vehicle for use with a medical practitioner network having as providers of the medical practitioner network a plurality of medical practitioners is provided. The system includes a seat and one or more sensors in the seat to detect biometrics of a person sitting in the seat. The person is a subscriber to the medical practitioner network. The system further includes a vehicle controller in communication with the one or more sensors to determine from the biometrics of the person whether the person requires medical attention. The system further includes a V2X transceiver to broadcast, in response to the vehicle controller determining from the biometrics of the person that the person requires medical attention, a request for assistance for the person to medical practitioners of the medical practitioner network who are near a location of vehicle during the broadcasting.

The one or more sensors may be piezoelectric sensors.

A method for a vehicle having an autonomous vehicle control system is provided. The method includes detecting, from one or more sensors in a seat of the vehicle, biometrics of a person sitting in the seat. The method further includes determining from the biometrics of the person, by a vehicle controller in communication with the one or more sensors, whether the person requires immediate medical attention. In response to the vehicle controller determining from the biometrics of the person that the person requires immediate medical attention, the autonomous vehicle control system is used, by the vehicle controller, to drive the vehicle to a medical facility.

The method may include determining from the biometrics of the person, by the vehicle controller, that the person requires immediate medical attention includes transmitting, via a transceiver of the vehicle, the biometrics of the person to a remote diagnostic facility for the remote diagnostic facility to analyze the biometrics of the person.

In response to the vehicle being driven to the medical facility because of the person requiring immediate medical attention, the method may further include transmitting to the medical facility and/or a physician of the person and/or a contact of the person, via a transceiver of the vehicle, the biometrics of the person to the medical facility and/or an indication that the person is being driven to the medical facility.

The one or more sensors may be piezoelectric sensors.

DETAILED DESCRIPTION

Detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of components. Therefore, specific structural and functional details disclosed herein are not to be interpreted as limiting, but merely as a representative basis for teaching one skilled in the art to variously employ the present invention.

Figure 1:
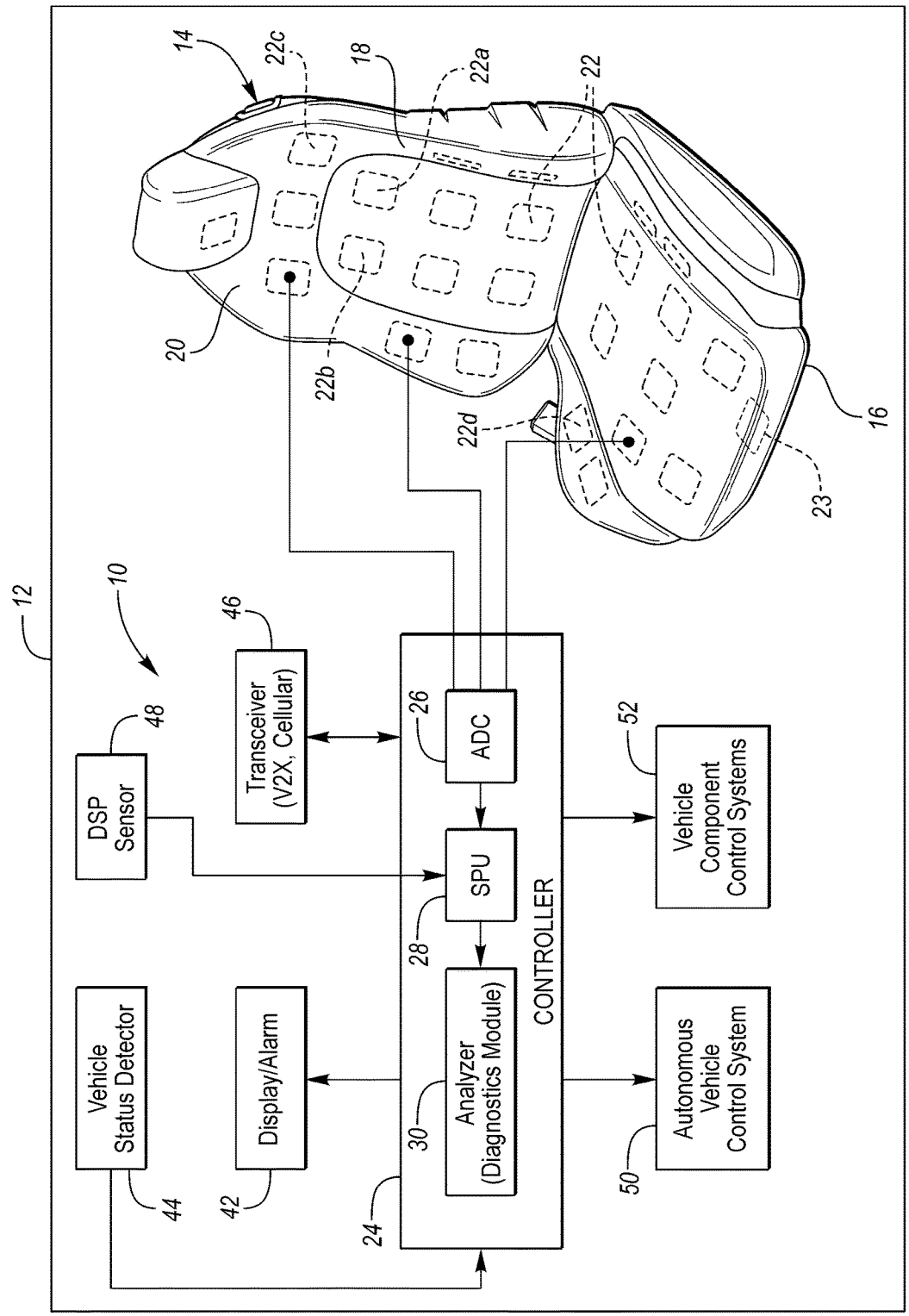
FIG. 1 illustrates a vehicle seating system including a perspective view of a vehicle seat of the vehicle seating system and a block diagram of other components of the vehicle seating system.

Referring now to FIG. 1, a vehicle seating system 10 is shown. Vehicle seating system 10 is implemented on a vehicle 12. Vehicle 12 may be a car, truck, or the like. Vehicle seating system 10 includes a seat 14. A perspective view of seat 14 is shown in FIG. 1.

Seat 14 includes a seat bottom (i.e., a seat cushion) 16 and a seat back 18. Seat bottom 16 is configured to support the sitting region of a person sitting in seat 14. Seat back 18 is configured to support the back of the person sitting in seat 14. Seat back 18 is pivotably connected to seat bottom 16 to extend upright relative to the seat bottom. Seat 14 further includes a cover 20 which covers or upholsters seat bottom 16 and seat back 18.

As shown in phantom in FIG. 1, seat 14 further includes an array of piezoelectric sensors 22. Due to its piezoelectric characteristics, each sensor 22 generates an electrical charge, response, or signal ("electrical signal") in response to mechanical stress applied on that sensor.

Biologically motivated force inputs of a person sitting in seat 14 cause mechanical stress on sensors 22. The biologically motivated force inputs include cardiac spatial displacements from the person's heart as the person's heart beats and respiratory spatial displacements from the person's lungs as the person inhales and exhales while breathing. Other force inputs of the person sitting in seat 14 causing mechanical stress on sensors 22 include voluntary movements of the person when the person moves to sit differently while sitting in seat 14. Involuntary movements of the person, such as twitching, are also force inputs causing mechanical stress on sensors 22.

The noted force inputs of the person sitting in seat 14 apply mechanical stress on sensors 22. Characteristics of the mechanical stress applied on sensors 22, such as the amount, position, force profile, duration, etc., correspond to the force inputs. Sensors 22 generate electrical signals in correspondence with the mechanical stress applied on the sensors. As the mechanical stress is in correspondence with the force inputs of the person sitting in seat 14, the electrical signals generated by sensors 22 are in correspondence with the force inputs of the person applied from the person to seat 14 and thereby applied to sensors 22. For instance, the electrical signals generated by sensors 22 in response to the mechanical stress applied on the sensors due to the person's heart beating are indicative of the person's heat beating.

Accordingly, the force inputs (e.g., heart beating, lungs inhaling and exhaling, intended movement, involuntary twitching, etc.) of the person can be deduced by analyzing the electrical signals of sensors 22. The heart and lungs of the person generate a displacement of the person's chest and abdominal cavity that introduces force inputs from the person to seat 14. These force inputs are applied to sensors 22 causing the sensors to generate electrical signals in response to the force inputs. As such, the person's heart can be monitored by analyzing the electrical signals generated by sensors 22 due to the mechanical stress applied on the sensors from displacement caused by the person's heart beating. The breathing of the person can be monitored by analyzing the electrical signals generated by sensors 22 due to the mechanical stress applied on the sensors from displacement caused by the person's lungs inhaling and exhaling.

The person's voluntary movement, such as the person moving from one seating position to another seating position while sitting in seat 14, also introduces force inputs from the person to seat 14. This type of movement involves voluntary, non-periodic muscle movements. The person's involuntary movement (e.g., the person twitching) while sitting in seat 14 introduces force inputs from the person to seat 14. The person's voluntary and involuntary movements can be monitored by analyzing the electrical signals generated by sensors 22 due to mechanical stress applied on the sensors from displacement caused by these movements.

Sensors 22 are distributed at respective locations across seat bottom 16 and seat back 18. Some of sensors 22 are positioned at respective locations on seat back 18 to be adjacent to the back side of the chest cavity of a person sitting in seat 14. These sensors 22 are collectively represented in FIG. 1, as an example, by sensors 22a and 22b. Sensors 22a and 22b are at respective locations on seat back 18 corresponding with cardiac anatomical locations of the person sitting in seat 14. The locations of sensors 22a and 22b in seat back 18 are optimized to gather cardiac and respiratory displacements based on greatest displacement. By being located at these positions on seat back 18 sensors 22a and 22b are subject to mechanical stress caused by cardiac spatial displacements of the person. Thus, the electrical signals generated by sensors 22a and 22b are primarily indicative of the cardiac (i.e., heart beating) and respiratory (i.e., lung inhaling and exhaling) actions of the person. Of course, sensors 22a and 22b can also detect voluntary and involuntary movements (e.g., twitching and/or fidgeting) of the person sitting in seat 14.

Other sensors 22 positioned at other respective locations on seat bottom 16 and/or seat back 18 are collectively represented in FIG. 1, as an example, by sensors 22c and 22d. Sensors 22c and 22d are at respective locations away from the cardiac anatomical locations of the person sitting in seat 14. The locations of sensors 22c and 22d on seat bottom and/or seat back 18 are optimized for detecting voluntary and involuntary movement of the person sitting in seat 14. Excessive movement or involuntary movement of the person sitting in seat 14 may be indicative of discomfort or pain of the person.

Sensors 22c and 22d are subject to mechanical stress caused by voluntary movement of the person sitting in seat 14 as the person moves and sits differently. For instance, sensors 22c and 22d are positioned on seat 14 to be subject to mechanical stress caused by movement of the person's extremities (e.g., the upper legs, buttocks, shoulder/upper arms, etc., of the person).

Sensors 22c and 22d are also subject to mechanical stress caused by involuntary movement (e.g., twitching and/or fidgeting) of the person, such as by the person's extremities, while the person is sitting in seat 14. Thus, the electrical signals generated by sensors 22c and 22d are primarily indicative of movement actions, voluntary and involuntary, of the person sitting in seat 14. Of course, sensors 22*c* and 22*d* can also detect cardiac and respiratory displacements of the person sitting in seat 14.

All sensors 22 are capable of detecting heart, respiration, and voluntary and involuntary movements. That is, sensors 22 are susceptible to movement of the person as well as the ballistocardiographic signature of the person's heart. Certain sensors 22 such as sensors 22*a* and 22*b* are optimized for detecting heart and respiration movements by being positioned near the cardiac and respiratory anatomical locations of the person sitting in seat 14. Other sensors 22 are optimized for detecting movement, for example, of the person's lower region by being positioned on seat bottom 16. However, from each individual sensor 22, independently of their positions, heart, respiration, and voluntary and involuntary movements can be derived.

Seat 14 further includes at least one other piezoelectric sensor 23. Sensor 23 is positioned at a respective location outside of the portions of seat bottom 16 and seat back 18 that are in contact with the person sitting in seat 14. For instance, sensor 23 may be on the lower frame, the tracks, etc., of seat 14 to be located at a position in which sensor 23 is unable to detect any of heart, respiration, and voluntary and involuntary movements of the person sitting in seat 14. As shown in FIG. 1, as an example, sensor 23 is on the bottom side of the frame of seat bottom 16 and therefore is not influenced by heart, respiration, and voluntary and involuntary movements of the person sitting in seat 14. As such, sensor 23 is strategically placed within the structure of seat 14 in one or more areas that are not susceptible to biological processes of the person. Thus, sensor 23 is isolated from biological force inputs while being susceptible to the same non-biological force inputs (i.e., noise such as vehicle noise, road noise, etc.) that the other sensors are susceptible. The electrical signal generated by sensor 23 is therefore indicative only of the noise. The electrical signal generated by sensor 23 can be used in signal processing to eliminate the noise from the electrical signals generated by the other sensors.

Sensor 23 thus functions as a noise sensor to be used for processing the electrical signals generated by the other sensors. The other sensors 22 (e.g., sensors 22*a*, 22*b*, 22*c*, 22*d*) generate electrical signals in response to mechanical stress applied on these sensors by movement (e.g., the person's heart beating, the person changing seating positions, the person twitching, etc.) of the person sitting in seat 14. Sensor 23 is affected by the same noise affecting the other sensors 22, but sensor 23 is not affected by movement of the person. In this way, the electrical signal generated by sensor 23 is indicative of the noise. The electrical signals generated by the other sensors in response to mechanical stress from the person include corresponding noise components. Thus, these noise components can be cancelled out from the electrical signals of the other components using the noise detected by sensor 23.

Piezoelectric sensors 22 are components of vehicle seating system 10. Vehicle seating system 10 employs sensors 22 to monitor or sense physiological or psychological attributes, conditions, and/or states (collectively "physiological state") of a person sitting in seat 14 of vehicle 12. That is, vehicle seating system 10 is a vital sign monitoring system for vehicle seating. As described, sensors 22 are part of an array of piezoelectric sensors which generate electrical signals in response to being mechanical stressed by biologically motivated force inputs such as respiratory and cardiac spatial displacements. Sensors 22 are integrated in seat bottom 16 and seat back 18 and function independently or in conjunction with one another to emphasize different force inputs. Sensors 22 are geometrically arranged within the structure of seat 14 to gather the force inputs from biological processes transmitted to the seat from the person sitting in the seat.

In being located at respective positions of seat bottom 16 and seat back 18, sensors 22 may be integrated into the trim, foam, and/or frame of seat 14 or freestanding between subcomponents of the seat (i.e., the sensors may be freeform within or between the trim, foam, and/or frame of the seat). Sensors 22 may be composed of basic piezoelectric materials, crystalline structures, smart fabric piezoelectric materials, and the like. Piezoelectric foam, fabrics, leathers and frames may form sensors 22 themselves. The piezoelectric sensing component, in addition to existing separate from core components, can be integrated within the core components via the use of piezoelectric foundations and materials, i.e., piezoelectric foam and textiles.

In other embodiments, any of sensors 22 may be embodied as piezo-resistive, pressure, capacitive, and Doppler sensors which generate electrical signals in response to mechanical stress applied on the sensors from biologically motivated force inputs of the person sitting in seat 14, displacement of the sensors caused from biologically motivated force inputs of the person sitting in the seat, and/or proximity detection by the sensors of the person sitting in the seat.

Vehicle seating system 10 further includes a controller 24. Controller 24 is an electronic hardware device such as a computer or processor. Controller 24 is connected to communication buses of vehicle 12. Controller 24 may be a vehicle controller of some sort that is a dedicated component of vehicle 12. Controller 24 includes sub-component electronic hardware devices in the form of an analog-to-digital converter (ADC) 26, a signal processing unit (SPU) 28, and an analyzer (or diagnostics module) 30 as shown in FIG. 1. Controller 24 includes other sub-component electronic hardware devices not shown in FIG. 1 for performing functions associated with vehicle seating system 10 including the functions described herein.

ADC 26 is in communication with sensors 22 to receive the electrical signals generated by the sensors. For instance, ADC 26 is connected to sensors 22 via electrical wires and the like. ADC 26 converts the electrical signals, which are in analog format, into digital format. SPU 28 receives the digitized electrical signals from ADC 26. SPU 28 performs signal corrections and calculations on the digitized electrical signals. SPU 28 provides the digitized electrical signals as further processed to analyzer 30. The digitized electrical signals from SPU 28 are clean electrical signals for analysis of bio-markers. Analyzer 30 analyzes the digitized electrical signals for biomedical assessment, identification, medical condition assessment, medical emergency assessment, etc., of the person sitting in seat 14 as described herein.

Figure 2:
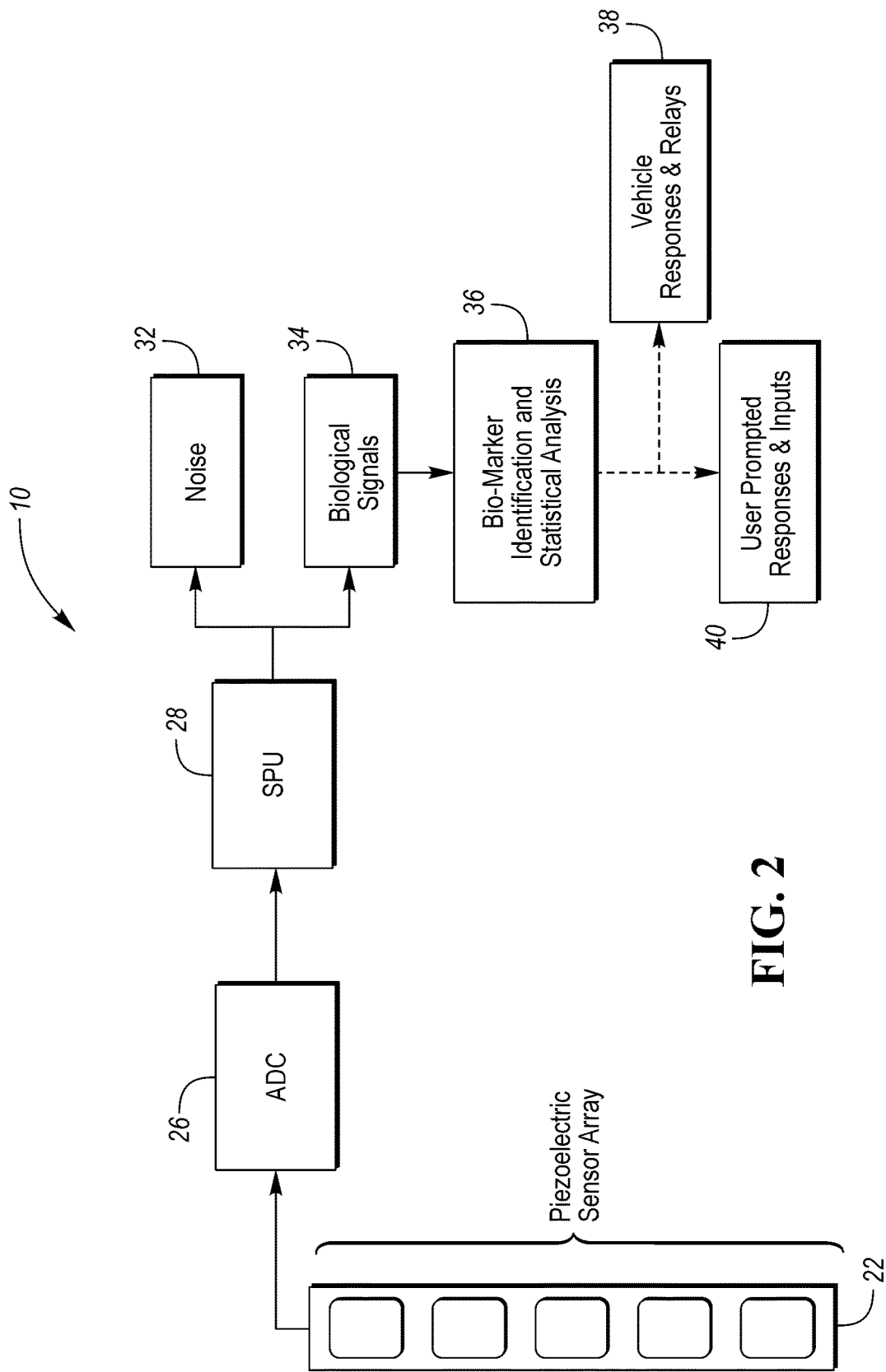
FIG. 2 illustrates a functional block diagram of the vehicle seating system.

Referring now to FIG. 2, with continual reference to FIG. 1, a functional block diagram of vehicle seating system 10 is shown. As described, sensors 22 have mechanical force (biological or noisy motion) applied to them from the person sitting in seat 14. Sensors 22 generate electrical signals due to the piezoelectric effect in correspondence with mechanical force applied on the sensors.

Each electrical signal generated by a sensor 22 includes an information component and a noise component. The information component is due to the mechanical stress applied on the sensor from the biologically motivated force inputs of the person sitting in seat 14. The noise component is due to mechanical stress applied on the sensor caused by, for instance, vibration of vehicle 12 and/or seat 14 as the vehicle is in operation.

ADC 26 of controller 24 receives the electrical signals generated by sensors 22 and provides digitized versions of the electrical signals to SPU 28 of controller 24. SPU 28 processes the digitized versions of the electrical signals to remove the noise component therefrom. The removed noise component from the electrical signals is identified as noise 32 in FIG. 2. The resulting electrical signals are clean electrical signals having just the information component. SPU 28 outputs the clean electrical signals, identified as biological signals 34 in FIG. 2, to analyzer 30 of controller 24.

Analyzer 30 analyzes biological signals 34 for various bio-marker information and statistical analysis as indicated by functional block 36. As described, biological signals 34 are indicative of biologically motivated force inputs of the person on sensors 22. That is, each biological signal 34 obtained from the electrical signal generated by a sensor 22 is indicative of biologically motivated force inputs on that sensor. The periodic nature of such biological vital inputs and the correlation between force applied and electrical signal response aid in the positive identification of these inputs. Accordingly, biological signals 34 are indicative, for instance, of "clean" respiratory and heart signatures. Analyzer 30 can thus analyze biological signals 34 to extract various vital criteria including heart rate, breathing rate, heart rate variability, etc.

Controller 24 may use the bio-marker information obtained by analyzer 30 and the statistical analysis performed by the analyzer in various ways. In general, controller 24 may control other components of vehicle seating system 10 and vehicle 12 as a function of the bio-marker information and/or statistical biological data analysis, as indicated by functional block 38. Controller 24 may interact with the person sitting in seat 14 as a function of the bio-marker information and/or statistical biological data analysis, as indicated by functional block 40.

Referring to FIG. 1, vehicle seating system 10 includes other components. The other vehicle seating system components include a display or alarm 42, a vehicle status detector 44, a wireless communications transceiver 46, one or more sensors 48 (labeled DSP sensor as in Digital Signal Processor sensor), an autonomous vehicle control system 50 (for the situation that vehicle 12 is an autonomous vehicle), and one or more other vehicle component control systems 52.

Display or alarm 42 is a configured to display information for persons in vehicle to view and generate an alarm for persons in vehicle to hear. Controller 24 can control display or alarm 42 to communicate status, commands, requests, etc., with the person sitting in seat 14 or other vehicle occupants and generate an alarm for the person or other vehicle occupants to advise of an alarm situation.

Vehicle status detector 44 is configured to monitor various conditions or statuses of vehicle 12. For instance, vehicle status detector 44 can detect vehicle 12 being in an accident, the vehicle being turned off, and the like. Controller 24 is in communication with vehicle status detector 44 to be apprised of any of the monitored conditions or statuses of vehicle 12.

Wireless communication transceiver 46 configured to wirelessly communicate with communication devices external to the vehicle 12. For instance, transceiver 46 may include a cellular transceiver operable to make cellular calls and/or a "V2X" transceiver to make calls from vehicle 12 to communication devices of other vehicles, infrastructure communication devices, communication devices of other persons, etc. (The V2X transceiver may be for vehicle to vehicle (V2V) communications, vehicle to infrastructure (V2I) communications, vehicle to pedestrian communications, etc.) Controller 24 is operable to employ transceiver 46 to make automatic communications with the communication devices of other vehicles, infrastructure communication devices, communication devices of other persons, etc.

DSP sensor 48 may include one or more accelerometers, gyroscopes, Doppler sensors, and the like. DSP sensor 48 is for use by SPU 28 of controller 24 in performing digital signal processing of the electrical signals from sensors 22. SPU 28 may perform DSP processing techniques on the digitized versions of the electrical signals of sensors 22 using the information from DSP sensor. In this way, SPU 28 employs adaptive filtering to clean up the electrical signals by removing non-biological impulses (e.g. noise) from the electrical signals.

Autonomous vehicle control system 50 is configured to autonomously control vehicle 12 in some manner. For instance, autonomous vehicle control system 50 may provide vehicle 12 with level three or level four autonomous vehicle capability, as defined by the National Highway Traffic Safety Administration (NHTSA) standards (the Society of Automotive Engineer (SAE) uses five level nomenclature). Level three autonomous vehicle capability enables the driver of vehicle 12 to cede full control of all safety critical functions under certain traffic and environmental conditions. In this case, the driver is available for occasional control. With level four autonomous vehicle capability, vehicle 12 is designed to perform all safety critical functions and monitor roadway conditions for an entire trip. In this case, the driver is not expected or required to be available to take control of vehicle 12 during the trip. Controller 24 is operable to activate autonomous vehicle control system 50 and instruct the autonomous vehicle control system to drive vehicle 12 to a location designated by the controller automatically or by any of the vehicle occupants.

Vehicle component control systems 52 include control systems such as the braking system of vehicle 12 and the flasher light system of the vehicle. Controller 24 is operable to activate vehicle component control systems 52. For instance, controller 24 may activate the flasher light system of vehicle 12 to generate an alarm for outsiders to come and investigate. Controller 24 may activate the braking system of vehicle 12 based on certain detected statuses (e.g., stress, fatigue, drowsiness, distraction) of the person sitting in seat 14 and the person is the driver of the vehicle (i.e., seat 14 is the driver vehicle seat).

As described, controller 24 is in communication with and can control or interact with each of display 42, vehicle status detector 44, transceiver 46, DSP sensor 48, autonomous vehicle control system 50, and vehicle component control system 52. Controller 24 uses the bio-marker information and the statistical biological data analysis from analyzer 30 in controlling or interacting with these other vehicle seating system components.

Controller 24 may use the bio-marker information and the statistical biological data analysis to control and/or interact with the other vehicle seating system components and/or the person sitting in seat 14 in the following various ways. First, as a general measure of biometric data for assessment of physiological and/or psychological status (e.g., stress, fatigue, drowsiness, distraction, etc.) of the person sitting in seat 14. The physiological and/or psychological status of the person sitting in seat 14 can particularly impact the operational safety of vehicle 12 when the person is the driver of the vehicle. Controller 24 may control and/or interact with the other vehicle seating system components and/or the person based on the detected physiological/psychological status of the person. In this way, vehicle seating system 10 can identify and react to stress/fatigue/discomfort etc. of the person to thereby increase safety of vehicle operation.

Second, as a life detection system for the prevention of loss of life of occupants, such as small children, animals, or disabled or elderly persons, left within stationary and unpowered vehicle 12 during dangerous conditions. Controller 24 can detect from vehicle status detector 44 whether vehicle 12 is stationary and unpowered, whether the windows of the vehicle are closed, the temperature inside the vehicle, the ambient temperature outside the vehicle, etc. Controller 24 uses the bio-marker information to detect whether a person is sitting in seat 14. In the case where a person is detected to be sitting in seat 14 and vehicle 12 is detected to be stationary and unpowered, controller 24 can trigger alarm 42, employ transceiver 46, trigger vehicle component control system 52 in the form of the flasher light, etc., to generate a warning, especially when high temperatures are detected, to request assistance from others to remedy the situation involving the person being left alone in the vehicle.

Third, as a means of critical assessment (triage) during emergency situations where vital sign data can be transmitted to first responders thereby increasing the likelihood of survival during such incidents. Controller 24 can detect from vehicle status detector 44 that vehicle 12 has been in an accident. Controller 24 obtains the biological status information generated by sensors 22 before, during, and after vehicle 12 has been in the accident. The biological status information includes vital sign information (e.g., heart rate, breathing rate, etc.) of the person sitting in seat 14. Controller 24 can employ transceiver 46 to communicate the vital sign information to first responders. In this way, vehicle seating system 10 provides an emergency response function and can be used as an assessment tool for vehicle occupants to determine vital sign activity and criticality of the situation (emergency triage). At the least, vehicle seating system 10 can be used as a relay of the number of patients to the first responders thereby allowing for optimal responder/patient ratios and communicate the vital measurements of the patients to the first responders as a pre-arrival triage tool. This assessment should improve response time for more critically injured vehicle occupants thus resulting in a greater likelihood of survival.

Fourth, as a long-term database of biomedical statistics that the person sitting in seat 14 may use to assess personal health and potentially share with their medical practitioners. Controller 24 may include a database for storing long-term biological status information of the person sitting in seat 14. In this way, vehicle seating system 10 can be used as a means for personal health tracking for vehicle occupants and their healthcare providers when sharing is desired.

Fifth, as a physical detector for discomfort or pain of the person sitting in seat 14. Analyzer 30 of controller 24 may determine from analyzing the biological status information of the person sitting in seat 14 that the person is in some sort of discomfort or pain. Controller 24 may react to this determination by providing some sort of advice or notification on display 42 regarding the detected discomfort or pain for the person to see, by adjusting the position of seat 14 to change the seating position of the person to try to alleviate the person's discomfort or pain, or by some other manner. In this way, vehicle seating system 10 can perform fidget detection and be used as a means of assessing discomfort or pain via non-periodic biological inputs (e.g., force inputs caused by twitching of the person sitting in seat 14).

Sixth, as a detector of occupant physiological make-up (e.g., size/mass) for safety system engagement. Analyzer 30 may determine from analyzing the biological status information of the person sitting in seat 14 whether the person is an adult or a child and the person's position in space inside the vehicle. In this way, vehicle seating system 10 can perform physiological make-up detection of the person sitting in seat 14.

As described, vehicle seating system 10 employs a multi-sensor array design of seat 14 to distinguish biological inputs of a person sitting in the seat from non-biological inputs. Vehicle seating system 10 directly uses seating technology to access, assess, and run statistical analysis of biological inputs such as heart and respiratory rates to compute bio-markers like heart rate variability and arousal for status consideration (stress, drowsiness, pain, etc.). Vehicle seating system 10 also focuses on non-periodic motion of the person (i.e., fidgeting). Vehicle seating system 10 is integrated with emergency response communication via transceiver 46 or other third-party application. Vehicle seating system 10 may also be integrated with life preserving methods for vehicle occupants that are incapable of self-protection. Vehicle seating system 10 is configured to cause some sort of auto-start, alarm, authority alert, etc., to notify others and request assistance as part of the life preserving methods. Vehicle seating system 10 provides full vehicle, multi-occupant simultaneous monitoring for emergency events, presence, and condition.

Figure 3:
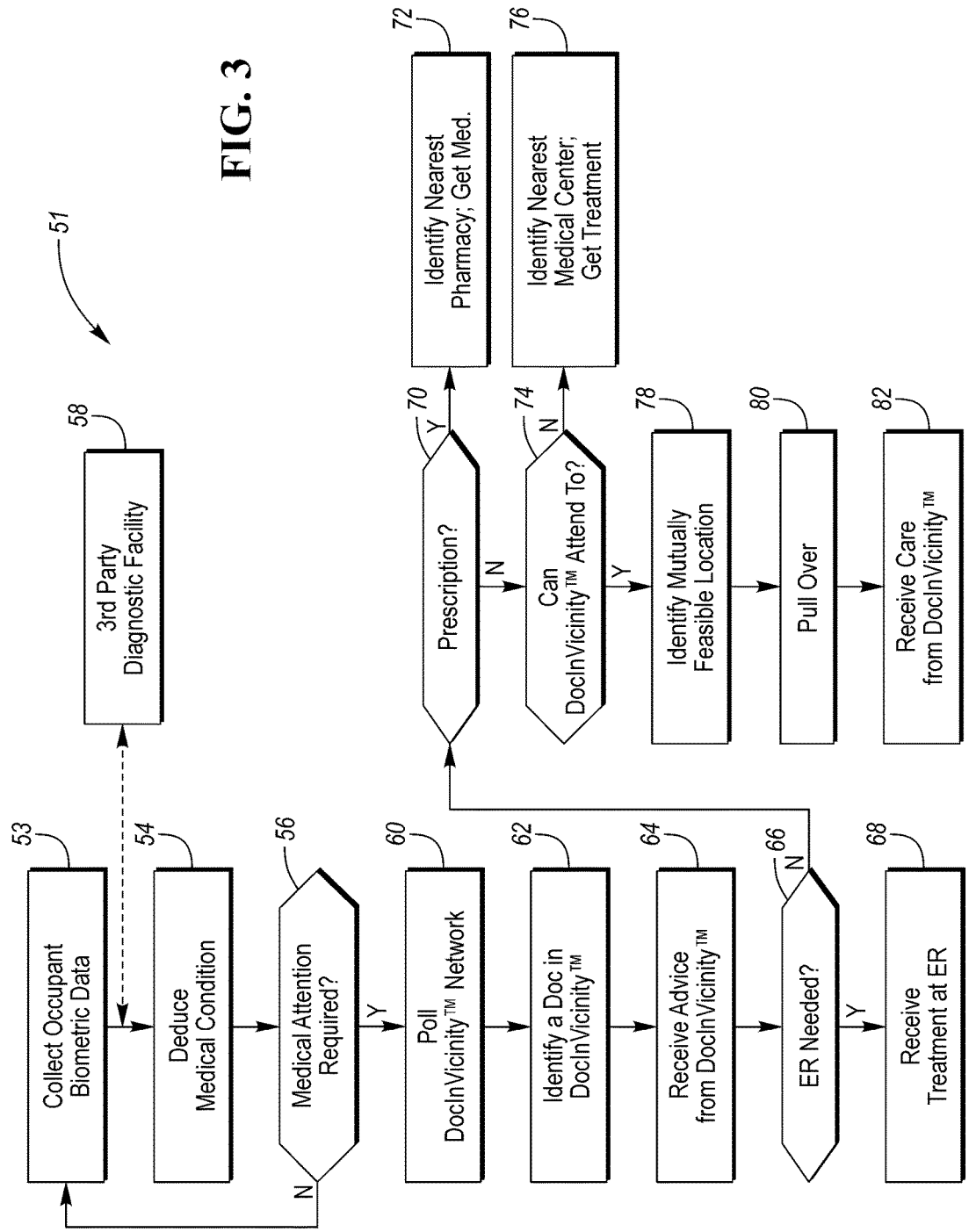
FIG. 3 illustrates a block diagram of a first operation process of the vehicle seating system.

Referring now to FIG. 3, with continual reference to FIG. 1, a block diagram of a first operation process 51 of vehicle seating system 10 is shown. First operation process 51 may be employed when transceiver 46 of vehicle seating system 10 is a V2X transceiver. First operation process 51 uses a safety system of seat 14, such as provided by controller 24 and sensors 22, in conjunction with V2X communications of transceiver 46 to communicate with medical practitioners (e.g., physicians) the biological status of the person sitting in the seat.

In operation, analyzer 30 of controller 24 analyzes the biological status of the person sitting in seat 14 from the electrical signal information generated by sensors 22. Analyzer 30 detects when the biological status information of the person indicates that the person requires medical attention. Controller 24 in turn causes transceiver 46 to communicate, via V2X, biological status information of the person, a request for assistance, the location of vehicle 12 to medical practitioners in the vicinity of vehicle 12 (i.e., to medical practitioners in other vehicles near vehicle 12, medical practitioner pedestrians near vehicle 12, and medical practitioners located in physician or hospital offices near vehicle 12), etc. A medical practitioner responding to the request can be apprised of the status of the person from the biological status information. The responding medical practitioner can act to provide medical assistance to the person based on the status of the person. In this way, first operation process 51 employs biometrics and V2X communications to consult a medical practitioner in the vicinity of the person in vehicle 12 for medical help for the person.

As shown in FIG. 3, first operation process 51 commences by collecting biometric data of the person sitting in seat 14, as indicated in block 53. The biometric data is provided by sensors 22. Alternatively, other ECG, and/or EEG in-seat or on-board sensors in vehicle 12 may be used to provide the biometric data. Analyzer 30 of controller 24 analyzes the biometric data to deduce the medical condition of the person, as indicated in block 54. Analyzer 30 determines from the deduced medical condition of the person whether a medical condition for the person exists, as indicated in decision block 56. Alternatively, the biometric data is periodically transmitted via transceiver 46 to a third-party diagnostic facility which analyzes the biometric data and diagnoses whether a medical condition for the person exists, as indicated in block 58.

Upon it being determined that a medical condition for the person in vehicle 12 exists, controller 24 causes transceiver 46 to use V2X communications to poll for medical practitioners in the vicinity of vehicle 12 with requests for assistance, as indicated in block 60. Each request for assistance at least includes a request that assistance of a medical practitioner be provided for an occupant of vehicle 12. Each request for assistance may further include the biological status information of the person, the location of vehicle 12, an indication of the severity of the need for assistance, and the like. Any of this additional information may be communicated as part of the broadcasted initial request for assistance or may be communicated individually to just the responding medical practitioners.

The person in vehicle 12 is a subscriber to a medical practitioner network. Medical practitioners are invited beforehand to join this network as medical service providers. Medical practitioners who opt into this network are to be apprised via V2X communications of persons in vehicles in need of medical attention and in the same geographic area as (i.e., preferably in the vicinity of or near) the medical practitioners. The medical practitioners are intended to respond to persons in need of medical attention. As such, transceiver 46 uses V2X communications to poll for medical practitioners in the medical practitioner network who are in the vicinity of vehicle 12. This medical practitioner network is indicated in FIG. 3 as the DocInVicinity™ network.

A medical practitioner who has received and has responded to the request for assistance is identified, as indicated in block 62. For instance, the medical practitioner communicates an acknowledgment receipt of the request for assistance via V2X communications to transceiver 46. The medical practitioner may also communicate the identity and contact information of the medical practitioner and the current location of the medical practitioner. The biological status information of the person is communicated via V2X transceiver to the medical practitioner. The medical practitioner analyzes the biological status information of the person to determine an appropriate course of action (e.g., a prescription, an ER visit, a pullover vehicle to be attended, etc.) for the person. The medical practitioner uses V2X communications to communicate to controller 24 via transceiver 46 a recommendation of the appropriate course of action for the person, as indicated in block 64.

Controller 24 processes the recommended course of action to determine whether an emergency room visit for the person is recommended by the responding medical practitioner, as indicated in decision block 66. If an emergency room visit for the person is recommended, then controller 24 uses display 42 to advise the driver of vehicle 12 (who may be the person requiring assistance) that the person needs to be taken to the emergency room, as indicated in block 68. In the case of autonomous vehicle control system 50 being available, controller 24 may instruct the autonomous vehicle control system to autonomously drive vehicle 12 to the emergency room.

Controller 24 processes the recommended course of action to determine whether a prescription for the person is recommended by the responding medical practitioner, as indicated in decision block 70. If a prescription for the person is recommended, then controller 24 uses display 42 to advise the person of the prescription recommended, as indicated in block 72. Controller 24 may also employ navigation information from a navigation system of vehicle 12 to identify and advise of the nearest pharmacy.

Controller 24 processes the recommended course of action to determine whether an in-person visit with a medical practitioner is recommended and whether the responding medical practitioner can handle the in-person visit, as indicated in decision block 74. If an in-person visit is recommended, but the responding medical practitioner cannot handle the in-person visit, then controller 24 uses the display 42 to advice the person that an in-person medical visit is recommended, as indicated in block 76. Controller 24 may also employ navigation information of vehicle 12 to identify and advise of the nearest medical practitioner treatment facility.

If an in-person visit is recommended and the responding medical practitioner can handle the in-person visit, then any of the vehicle occupants, controller 24, and/or an appropriate vehicle component control system 52 and the responding medical practitioner can communicate using V2X communications to identify a mutually feasible location to meet, as indicated in block 78. The driver of vehicle 12 then drives the vehicle to the designated pull over location, as indicated in block 80. In the case of autonomous vehicle control system 50 being available, controller 24 may instruct the autonomous vehicle control system to autonomously drive vehicle 12 to the designated pull over location. The responding medical practitioner meets with the person at the designated pull over location to provide care to the person, as indicated in block 82.

Additionally, in response to any of the recommended courses of action and advice from the responding medical practitioner via the V2X communications, the person that is the subject of the recommended course of action can choose other options. For instance, the person can choose to go to a medical facility, deny the medical attention, choose to visit a primary care physician instead of the responding medical practitioner, indicate that family and other designated contacts be notified of the recommended courses of action communicated to the person, and the like. Further, medical practitioners in the vicinity of vehicle 12 and non-practitioners who subscribe to the service to receive medical help can opt-in or opt-out of the ability to communicate with occupants of other vehicles who subscribe to the service.

Figure 4:
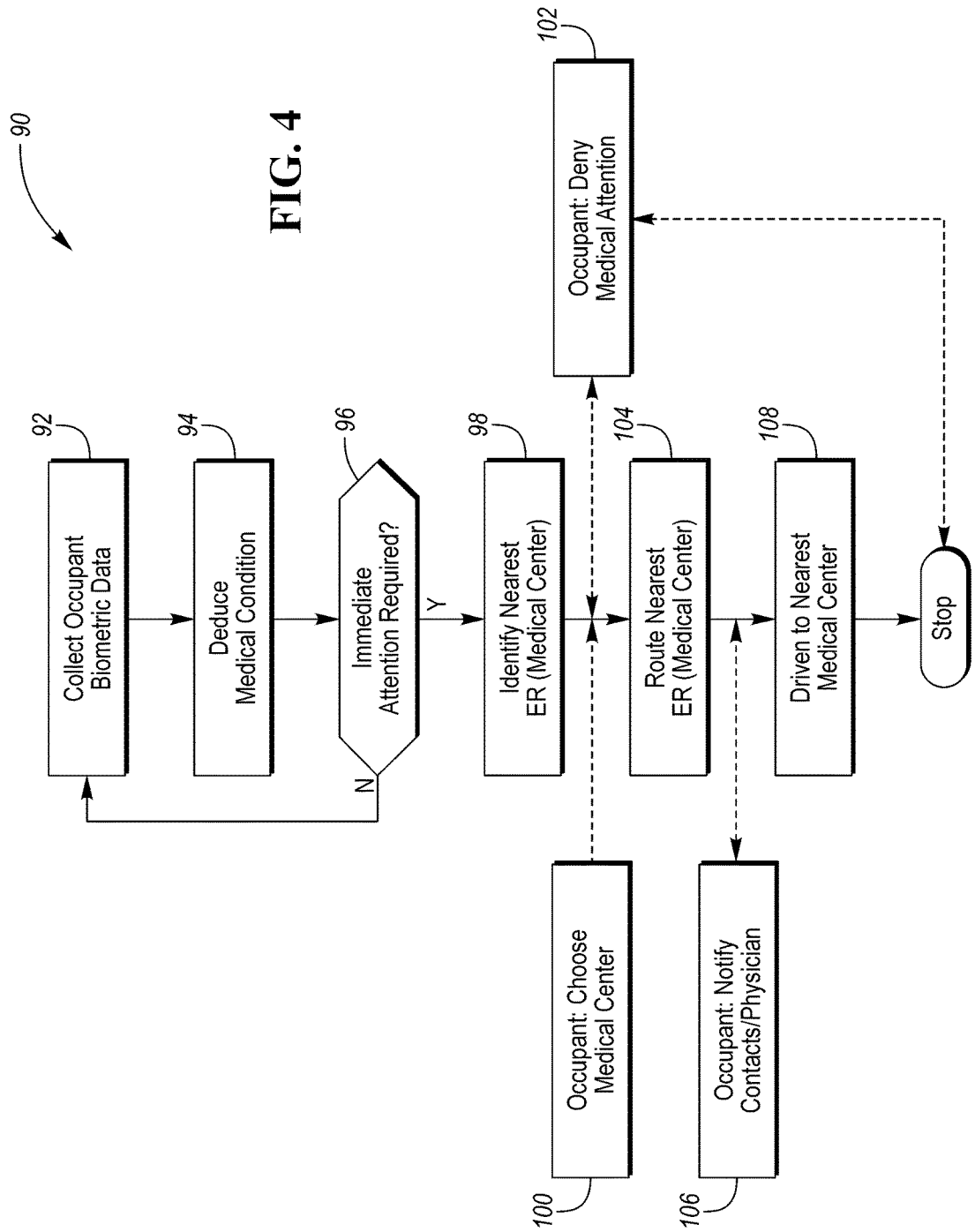
FIG. 4 illustrates a block diagram of a second operation process of the vehicle seating system.

Referring now to FIG. 4, with continual reference to FIG. 1, a block diagram of a second operation process 90 of vehicle seating system 10 is shown. Second operation process 90 may be employed when autonomous vehicle control system 50 is part of vehicle seating system 10. Second operation process 90 uses a safety system of seat 14, such as provided by controller 24 and sensors 22, in conjunction with autonomous vehicle control system 50 to autonomously drive vehicle 12 to a medical facility upon determining from the biological status of the person sitting in seat 12 that the person requires medical attention.

In operation, analyzer 30 of controller 24 analyzes the biological status of the person sitting in seat 14 from the electrical signal information generated by sensors 22. Analyzer 30 detects when the biological status information of the person indicates that the person requires medical attention. Controller 24 in turn causes autonomous vehicle control system 50 to drive vehicle 12 to a medical facility when it is determined that the person requires medical attention. In this way, second operation process 90 employs biometrics and autonomous driving to drive vehicle 12 to a medical facility near vehicle 12 upon detecting that person in seat 14 of vehicle 12 requires medical attention.

As shown in FIG. 4, second operation process 90 commences by collecting biometric data of the person sitting in seat 14, as indicated in block 92. The biometric data is provided by sensors 22. Alternatively, other ECG and/or EEG in-seat or on-board sensors in vehicle 12 may be used to provide the biometric data. Analyzer 30 of controller 24 analyzes the biometric data to deduce the medical condition of the person, as indicated in block 94. Analyzer 30 determines from the deduced medical condition of the person whether immediate medical attention for the person is required, as indicated in decision block 96.

Upon it being determined that immediate medical attention for the person is required, controller 24 uses navigation system information to identify the nearest medical facility, such as an emergency room, as indicated in block 98. Controller 24 may control display 42 to advise the person that the person requires immediate medical attention and to advise of the nearest medical facility. The person or another occupant of vehicle 12 may use a human-machine interface (HMI) device connected to controller 24 to advise the controller of a different medical facility to be chosen, as indicated in block 100. The person or other occupant of vehicle 12 may use the HMI device to advise controller 24 that the person does not want the medical attention and that the vehicle is not to be driven to the nearest medical facility, as indicated in block 102.

Second operation process 90 continues with controller 24 using the navigation system information to identify a route to the nearest or chosen medical facility, as indicated in block 104. Controller 24 may also communicate via transceiver 46 to notify the contacts and physician of the person that the person requires medical attention, the biological status information of the person, and/or the fact that the person will be driven (or will drive) to the identified medical facility, as indicated in block 106. This communication may be conducted via V2X communications and/or wireless communications such as cellular or satellite communications. Controller 24 then controls autonomous vehicle control system 50 to drive vehicle 12 to the identified medical facility along the identified route, as indicated in block 108.

While exemplary embodiments are described above, it is not intended that these embodiments describe all possible forms of the present invention. Rather, the words used in the specification are words of description rather than limitation, and it is understood that various changes may be made without departing from the spirit and scope of the present invention. Additionally, the features of various implementing embodiments may be combined to form further embodiments of the present invention.

What is claimed is:

1. A method for a vehicle, comprising:
establishing a medical practitioner network having as a subscriber to the medical practitioner network a person that is sitting in a seat of the vehicle and having as providers of the medical practitioner network a plurality of medical practitioners;
detecting, from one or more sensors in the seat of the vehicle, biometrics of the person;
determining from the biometrics of the person, by a vehicle controller in communication with the one or more sensors, whether the person requires medical attention; and
in response to the vehicle controller determining from the biometrics of the person that the person requires medical attention, broadcasting, from a V2X transceiver of the vehicle, a request for assistance for the person to medical practitioners of the medical practitioner network who are near a location of vehicle during the broadcasting.

2. The method of claim 1 further comprising:
broadcasting with the request for assistance, from the V2X transceiver, the location of the vehicle.

3. The method of claim 1 further comprising:
broadcasting with the request for assistance, from the V2X transceiver, the biometrics of the person.

4. The method of claim 1 further comprising:
receiving, by the V2X transceiver, a response from a medical practitioner responding to the request for assistance.

5. The method of claim 4 further comprising:
transmitting to the responding medical practitioner, by the V2X transceiver, the location of the vehicle.

6. The method of claim 4 further comprising:
transmitting to the responding medical practitioner, by the V2X transceiver, the biometrics of the person.

7. The method of claim 6 further comprising:
receiving, by the V2X transceiver, a recommended course of action from the responding medical practitioner; and
communicating the recommended course of action, by the vehicle controller, to the person.

8. The method of claim 7 wherein the vehicle has an autonomous vehicle control system and the recommended course of action is that the person be taken to an emergency room, the method further comprising:
using the autonomous vehicle control system, by the vehicle controller, to drive the vehicle to an emergency room.

9. The method of claim 7 wherein the recommended course of action is a prescription for the person, the method further comprising:
employing navigation information from a navigation system of the vehicle, by the vehicle controller, to advise the person of pharmacies near the location of the vehicle.

10. The method of claim 7 wherein the recommended course of action is an in-person visit with the responding medical practitioner, the method further comprising:
communicating between the person and the responding medical practitioner a mutually feasible location to meet.

11. The method of claim 1 wherein:
determining from the biometrics of the person, by the vehicle controller, that the person requires medical attention includes transmitting, via a transceiver of the vehicle, the biometrics of the person to a remote diagnostic facility for the remote diagnostic facility to analyze the biometrics of the person.

12. The method of claim 1 wherein:
the one or more sensors are piezoelectric sensors.

13. A system for a vehicle for use with a medical practitioner network having as providers of the medical practitioner network a plurality of medical practitioners, the system comprising:
a seat;
one or more sensors in the seat to detect biometrics of a person sitting in the seat, wherein the person is a subscriber to the medical practitioner network;

a vehicle controller in communication with the one or more sensors to determine from the biometrics of the person whether the person requires medical attention; and a V2X transceiver to broadcast, in response to the vehicle controller determining from the biometrics of the person that the person requires medical attention, a request for assistance for the person to medical practitioners of the medical practitioner network who are near a location of vehicle during the broadcasting.

14. The system of claim 13 wherein:
the one or more sensors are piezoelectric sensors.

15. A method for a vehicle having an autonomous vehicle control system, the method comprising:
detecting, from one or more sensors in a seat of the vehicle, biometrics of a person sitting in the seat;
determining from the biometrics of the person, by a vehicle controller in communication with the one or more sensors, whether the person requires immediate medical attention; and
in response to the vehicle controller determining from the biometrics of the person that the person requires immediate medical attention, using the autonomous vehicle control system, by the vehicle controller, to drive the vehicle to a medical facility.

16. The method of claim 15 wherein:
determining from the biometrics of the person, by the vehicle controller, that the person requires immediate medical attention includes transmitting, via a transceiver of the vehicle, the biometrics of the person to a remote diagnostic facility for the remote diagnostic facility to analyze the biometrics of the person.

17. The method of claim 15 further comprising:
in response to the vehicle being driven to the medical facility because of the person requiring immediate medical attention, transmitting to the medical facility, via a transceiver of the vehicle, the biometrics of the person to the medical facility and/or an indication that the person is being driven to the medical facility.

18. The method of claim 15 further comprising:
in response to the vehicle being driven to the medical facility because of the person requiring immediate medical attention, transmitting to a physician of the person, via a transceiver of the vehicle, the biometrics of the person to the medical facility and/or an indication that the person is being driven to the medical facility.

19. The method of claim 15 further comprising:
in response to the vehicle being driven to the medical facility because of the person requiring immediate medical attention, transmitting to a contact of the person, via a transceiver of the vehicle, the biometrics of the person to the medical facility and/or an indication that the person is being driven to the medical facility.

20. The method of claim 19 wherein:
the one or more sensors are piezoelectric sensors.

* * * * *